United States Patent [19]
Pickard et al.

[11] 3,993,640
[45] Nov. 23, 1976

[54] TREATMENT OF CELLULOSIC MATERIALS

[75] Inventors: Keith John Pickard, Widnes; Alan Smith, Tarvin, both of England

[73] Assignee: Laporte Industries Limited, London, England

[22] Filed: Dec. 9, 1974

[21] Appl. No.: 530,964

[30] Foreign Application Priority Data
Dec. 21, 1973   United Kingdom............... 59301/73

[52] U.S. Cl................................... 536/30; 8/115.6; 8/181; 8/189; 162/158; 252/182; 260/29.6 H; 260/326 A; 536/31
[51] Int. Cl.$^2$.................. C07D 209/34; C09K 3/00; D21F 11/00
[58] Field of Search........... 260/213, 326 A, 29.6 H, 260/212; 8/115.6, 181, 189; 162/158; 252/182

[56] References Cited
UNITED STATES PATENTS

| | | | |
|---|---|---|---|
| 2,594,145 | 4/1952 | Flory................................. | 260/213 |
| 2,961,367 | 11/1960 | Weisgerber....................... | 162/158 |
| 3,034,922 | 5/1962 | Boe..................................... | 162/158 |
| 3,084,092 | 4/1963 | Arlt..................................... | 8/189 |
| 3,236,685 | 2/1966 | Caldwell et al..................... | 8/115.6 |
| 3,562,100 | 2/1971 | Wasko et al........................ | 162/158 |
| 3,575,796 | 4/1971 | Brown et al........................ | 162/158 |
| 3,878,224 | 4/1975 | Matsui et al....................... | 260/326 A |

FOREIGN PATENTS OR APPLICATIONS

1,274,654   5/1972   United Kingdom................ 162/158

*Primary Examiner*—Ronald W. Griffin
*Attorney, Agent, or Firm*—Larson, Taylor and Hinds

[57] ABSTRACT

The present invention provides compositions for treating cellulosic materials, and in particular for sizing paper or waterproofing textiles with a reactive agent. The reactive agent is a cyclic imide substituted by an aliphatic hydrophobic group and N-substituted by an electron-withdrawing group. Preferably, the composition contains a non-aromatic cyclic imide N-substituted by a long chain acyl group, e.g. N-stearoyl-4-cyclohexene-1,2-dicarboximide. Aqueous emulsions of the imides preferably contain a retention aid such as acrylamides and may be used particularly suitably to size aqueous paper pulp even under mildly alkaline conditions.

19 Claims, No Drawings

TREATMENT OF CELLULOSIC MATERIALS

The present invention relates to treatment of cellulosic materials, more specifically to sizing paper and to waterproofing textiles, and to the provision of agents therefor.

It has been recognised hitherto that methods of treating cellulosic materials, in which the material is treated with an agent with which it can be bonded chemically, could offer significant advantages over processes in which the treatment agent was held in place by merely physical attractions such as by Van der Waals forces. Consequently there have been various proposals involving the use of chemical compounds containing a reactive group capable of reacting with cellulosic hydroxyl groups. We have now discovered that one such reactive group is cyclic imides N-substituted by an electron-withdrawing group. In order to size or waterproof, the cyclic imide must also be substituted by a hydrophobic group.

According to one aspect of the present invention there is provided a process for treating cellulosic materials comprising the step of contacting the cellulosic material with a dispersion of a cyclic imide substituted by an aliphatic hydrophobic group and N-substituted by an electron-withdrawing group at a temperature sufficiently high for reaction to occur with the cellulosic material.

In certain embodiments of the invention the substituted cyclic imide may be represented by the general formula

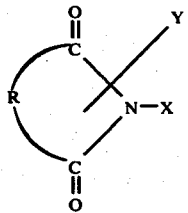

wherein R represents a diradical completing an imide ring having 6 or preferably 5 members, X represents an electron-withdrawing group and Y represents a hydrophobic aliphatic radical. It is to be understood that X and Y may form a single substituent at the N atom, i.e. form >N — X — Y.

Desirably R may be a dimethylene or a trimethylene diradical, optionally substituted by one or more aliphatic radicals. The aliphatic radicals may combine with the dimethylene or trimethylene carbon atoms to complete a ring, which may be carbocyclic. Suitably R may comprise a six-membered ring such as a cyclohexane or cyclohexene or such a diradical bridged across the 3–6 positions by a methylene group or oxygen atom. R, when a ring or otherwise, may be ethylenically unsaturated and may be substituted by one or more hydrophobic aliphatic groups. Although R may comprise an aromatic ring, optionally suitably substituted, we have achieved better results when R was non-aromatic. Thus, according to a preferred aspect of the invention, the cyclic imides may be represented by the above general formula wherein R is a non-aromatic, and X and Y are as hereinbefore defined.

It is to be understood that the electron-withdrawing group must be so positioned that it is able to withdraw electrons from the nitrogen atom of the cyclic imide. Typically the electron-withdrawing group may be a carbonyl group adjacent to the nitrogen atom. Preferably the carbonyl group links the cyclic imide to the hydrophobic aliphatic group.

Thus, according to a particular aspect of the invention there are provided N-acyl cyclic imides containing a hydrophobic aliphatic group, particularly non-aromatic cyclic imides.

Suitably the aliphatic hydrophobic group may be a hydrocarbon group. The hydrophobicity of the aliphatic group depends to a large extent upon the number of carbon atoms in a single chain in the group, the larger the number the greater the hydrophobicity up to about 22 carbon atoms. The number of carbon atoms is suitably at least 12, advantageously at least 16, desirably up to about 26.

Although the nitrogen atom may be substituted by short chain acyl groups such as acetyl, the acyl group preferably contains a long chain of at least 12 carbon atoms. Particularly the acyl group is palmitoyl, stearoyl or behenoyl, or their counterparts which are unsaturated, for example those derived from oleic and linoleic acids, because such acyl groups are both electron-withdrawing and hydrophobic.

Eminently suitable cyclic imides for imparting water repellancy are succinimide, cyclohexane-1,2-dicarboximide and 4-cyclohexene-1,2-dicarboximide each N-substituted by a stearoyl, palmitoyl or behenoyl group, and other suitable cyclic imides includes similarly N-substituted glutarimide and 3,6-endoxo-4-cyclohexene-1,2-dicaboximide. Any of the aforementioned cyclic imides may be substituted by an alkyl group from $C_1$ to long chain groups such as palmityl or stearyl.

The term "dispersion" is used herein to denote both solutions in compatible organic liquids, and aqueous emulsions.

Compositions for treating the cellulosic material may be prepared by dissolving the imide in a non-reactive organic liquid. The term "non-reactive organic liquid" indicates that an organic liquid is chosen which is unreactive towards the imide and the cellulosic material. Such a liquid is free of hydroxyl and amino groups, so that methanol, for example, is unsuitable whereas hydrocarbons, halocarbons or halohydrocarbons, such as benzene, toluene, dichloromethane or carbon tetrachloride and aliphatic esters and ketones are suitable. Preferred liquids have a boiling point of less than about 150° C, and more preferred below 100° C, so that removal from the cellulosic material by evaporation is rendered easier and requires less energy.

Compositions, especially formulated for sizing an aqueous paper stock, but which can also be used to treat the other cellulosic materials, can be prepared by emulsifying the cyclic imides herein described with water. Desirably the emulsion may also contain a retention aid, which is usually a cationic polyelectrolyte or is anionic or nonionic. Suitably the weight ratio of the total amount of retention aid to imide is from about 2:1 to 1:50 preferably 2:1 to 1:20. Suitable retention aids include cationic organic polymers as described in British Pat. Specification No. 1274654, in particular cationic starches therein, and also polyacrylamides, optionally copolymerised with unsaturated amine salts and polyamides generally, including polyamide-polyamines and polyethylene-imines, and epichlorhydrin condensates of each. It is believed that such retention aids, whilst not chemically reacting with the cellulosic material themselves, act so as to bring the cyclic imide into intimate contact with the material, so that the amount of imide required to give a certain level of sizing falls, even to about half the quantity required in the absence of the retention aid.

The aqueous emulsion may contain an emulsifying agent in a weight ratio to the cyclic imide of from 1:1 to 1:50 preferably from 1:2 to 1:50. Suitable emulsifying agents are described in German Pat. application No. 2307512 (Laporte Industries) in the paragraph bridging pages 6 and 7 of the specification and the information contained therein is expressly imported into the present specification.

One of the effects of increase in the concentration of the sizing agent, retention aid and/or emulsifying agent is increase in the viscosity of the emulsion. Obviously for minimum storage and transport costs the concentration of the emulsion should be as high as possible and in practical terms should be balanced against the disadvantages of increased viscosity and hence poorer flow properties. Generally, the aqueous emulsion contain from 1 to 10 percent by weight of sizing agent, from 0 to 5 percent by weight of emulsifying agent and from 0.03 to 10 percent by weight of retention aid, the weight ratios of size to emulsifying agent and retention aid being selected so as to satisfy the ratios hereinbefore described.

Suitably the cellulosic material may contain cellulose or regenerated cellulose, such as cotton, linen or rayon or mixtures thereof or, typically, paper. Advantageously the paper may be in the form of aqueous paper stock which suitably may have been produced by any conventional process, for example mechanical pulp, semichemical pulp, or chemical pulp. The paper or pulp may be bleached, semibleached or unbleached, and may contain fillers or pigments such as clays, for example kaolin, calcium carbonate, titanium dioxide or zinc oxides. Conventionally aqueous paper stock is contacted with size in the form of an aqueous emulsion. Retention aids such as the polyamides or polyacrylamides may be added to the pulp separately from the emulsion, and preferably thereafter not subjected to high shear. Advantageously, the emulsions may be contacted with the pulp under moderately acidic conditions through neutral to slightly alkaline conditions, i.e. from about pH 4 to 10. Preferably a pH of from 7 to 9, is used to enable fillers like calcium carbonate to be employed and to avoid inferior ageing and strength properties which paper produced under acidic conditions tends to show.

Suitably the cellulosic material in the form of dried sheets or rolls may be treated by any conventional process used to impregnate fibrous materials. Thus, dried sheets or rolls of paper or other cellulosic material such as a textile cloth may be passed through a bath containing a solution of the cyclic imide in a compatible organic solvent, as hereinbefore described. The concentration of the cyclic imide in the solution and the amount of solution absorbed by the substrate govern the addition level of cyclic imide to the substrate; a high proportion of the cyclic imide actually reacts with the cellulose. Alternatively the bath may contain an aqueous emulsion of the cyclic imide. The amount of the composition absorbed by the sheets or rolls may be controlled by conventional methods such as the use of squeeze rollers. Other suitable methods of impregnation include brushing, spraying and roller-coating.

After contact between compositions containing the cyclic imide and the cellulosic material the material is dried. The temperature of the drying stage is selected so as not to damage the material, but is typically in excess of about 50° C, for example paper is often dried at from about 70° to 120° C., textiles from 100° to 150° C. Preferably the dispersion is used in such an amount and of such concentrations that the waterproofed textile or sized paper, when dry contains the minimum weight percentage of cyclic imide, to give as effective a waterproofing or sizing as is required.

One of the effects of variation of the diradical R in the cyclic imide is variation in the length of time the emulsion may be stored without a significant or excessive loss of its ability to size. Maleimide and like ethylenically unsaturated cyclic imides ought preferably not to be employed in aqueous emulsions because they lose their sizing ability too rapidly. In certain aspects of the present invention there is provided an aqueous emulsion containing succinimide or like imides in which the dimethylene group is replaced by a six-membered ring, N-acylated with an hydrophobic group, which may be stored for several months, which requires only small amounts of cyclic imide of the order of 0.3 percent or less to achieve an adequate sizing of paper, and which is capable of so sizing reasonably quickly at a temperature of no more than 110° C.

Cyclic imides are believed to be capable of reacting with cellulose, provided that sufficiently forcing conditions are provided. In order to react at a temperature of below 150° C, i.e. below the highest temperature at which textiles are normally dried, we believe that it is necessary for the imide ring to be activated. This may be achieved by substituting the imide ring at the nitrogen atom with an electronwithdrawing group such as an acyl group. It is believed that the effect may be enhanced by introducing strain into the imide ring, as for example in N-substituted-4-cyclohexene 1,2-dicarboximide. Activation of the cyclic imides towards reaction with cellulose will also, it is felt, result in activation towards reaction with water. Excessive activation, as in maleimide and like cyclic imides, can result in aqueous emulsions which have poor stability, but it must be understood that such imides can be applied successfully from solution in non-reactive organic liquids.

At least some of the N-acyl substituted cyclic imides may be prepared by following the general method described by Rothman, Serota and Swern in Volume 29 of the Journal of Organic Chemistry pages 646 to 650, published in March 1964 and making appropriate variations in the reactants. Briefly, the method entails fusion of a chosen cyclic imide with a selected enol ester, for example the fusion of succinimide with isopropenyl stearate to form N-stearoyl succinimide. The preparation of certain N-lauroyl and N-stearoyl cyclic imides was disclosed in the Rothman paper but there was no disclosure as to any use to which they could be put.

We have found a new or improved process for preparing an N-acylated cyclic imide comprising the steps of reacting a cyclic imide with a long chain acyl chloride and a tertiary amine in solution at an elevated temperature, and recovering N-long chain acylated cyclic imide therefrom. Tertiary amine hydrochloride forms as a by-product.

A preferred solvent dissolves both reactants and the N-acylated cyclic imide, but does not dissolve the tertiary amine hydrochloride. Such a preferred solvent is dichloropropane. Conveniently the tertiary amine may be triethylamine. The reaction may be carried out conveniently at a temperature of from 0° to 100° C, preferably from 40° C to 60° C during precipitation of tertiary amine hydrochloride, which generally takes about 10 minutes after addition of all the acyl chloride and filtration solution is preferably maintained at the reaction temperature. The precipitate may be washed well using fresh solvent, i.e. dichloropropane. The N-acylated cyclic imide may conveniently be recovered by evaporation using, for example, a rotary evaporator, and purified by recrystallisation of the residue from acetone or 60° – 80° petroleum spirit. N-Long chain-acylated cyclic imides may be prepared by this process, the preparation of N-stearoyl-4-cyclohexene-1,2-dicarboximide being typical.

Consequently, save as described in the said paper by Rothman et al, according to a further aspect of the present invention there are provided cyclic imides substituted by an aliphatic hydrophobic group and N-substituted by an electronwithdrawing group. In another aspect of the invention there are also provided compositions comprising an aqueous emulsion of cyclic imides substituted by an aliphatic hydrophobic group and N-substituted by an electron-withdrawing group.

It may also be apparent that the substituted cyclic imides as described herein may be used to coat or size materials which lack reactive groups and under such circumstances the material will be rendered water repellant in an analogous way to known non-reactive coating agents such as waxes, waxy aliphatic alcohols or amines having molecular weights of approximately 150 or more.

Various embodiments of the present invention will now be described more fully by way of Example.

In each of Examples 1 to 5 the cellulosic material to be treated (sized), comprised paper handsheets, made in a Mavis British Standard pulp evaluation apparatus (sold by H. E. Messmer in London), from a bleached sulphite pulp beaten to a freeness of 35° as measured by the Schopper Riegler test. 2 Litres of pulp having a cconsistency of 0.6 percent and a desired pH were disintegrated for 1800 revolutions, the size was added and the pulp disintegrated for a further 1800 revolutions. When a retention aid other than a cationic starch was used, it was added 250 revolutions of the disintegrator after the size addition, and disintegration was continued for a further 1550 revolutions. After the period of disintegration, aliquots of 200 mls of pulp were transferred to the handsheet machine in which the water had previously been adjusted to the desired pH. Sheets were then prepared using the standard procedure, and were dried and cured by heating on a rotary drum drier for 2.5 minutes or 8.75 minutes each at a temperature of 110° C, except where otherwise stated. After half an hour, when the sheets were conditioned under the standard conditions of 20° C 65 percent RH, the sizing of the sheets was tested using the Cobb Test. In the Cobb Test sheets are contacted with water for a selected period, 1 minute herein, and the result is expressed in grams of water absorbed per square meter of paper. Clearly, the lower the value the more effective has been the sizing. The term "addition level" used in the Tables is given by the formula Vc/W where V is the volume of emulsion or solution used, in liters, c is the concentration in grams/liter of cyclic imide therein and W is the weight in grams of fibre (when oven-dried) in the paper or pulp sized. The amount of size in the oven dried paper will in general be lower than the additional level when aqueous emulsions are employed, due to incomplete retention of the size.

In the Examples the figures quoted for retention aids other than cationic starch are the percentages by weight of active ingredient added, based on the weight of fibre in the oven dried paper, and for the cationic starch is the percentage weight of the starch composition on the same basis.

In Example 1 Emulsion B and in Example 4, Solutions SA and SB are present by way of comparison only. The remaining emulsions and solutions in the Examples are according to the present invention.

EXAMPLE 1

Each of emulsions A to AA were prepared using the following general method. First the size and emulsifying agents were dissolved in 15 ml of dry acetone, which was then mixed with 50 mls of water or 50 mls of a solution of a cationic starch using an emulsifier sold by Kinnematica GmbH under the Trade Name of POLYTRON PT 2000. Any other retention aid was added after emulsification with water or starch had been completed, by for example agitation for at least 2 minutes.

Various commercial products were used as retention aids or emulsifying agents in the emulsions, for the sake of convenience. Obviously these products could be replaced by other products falling within the general classes of compounds described hereinbefore. The emulsifying agents E1 and E2 were respectively sorbitan monopalmitate and polyoxyethylene (20) sorbitan monopalmitate, sold by Honeywill Atlas Limited under the Trade Names of, respectively, SPAN 40 and TWEEN 40.

Emulsifying agent E3 was a condensate of coconut fatty amine with ethylene oxide, sold by Lankro Chemicals Limited under the Trade Name of ETHYLAN TC.

Emulsifying agent E4 was cetyl pyridinium bromide. Retention aid R1 was a 50% by weight aqueous solution of cationic resin condensate of amide, base and formaldehyde, sold by I.C.I. Limited under the Trade Name of PERMINAL FC-P. Retention aid R2 was a 23 percent by weight aqueous solution of a cationic retention aid sold by J. Crosfield & Sons under the Trade Name of PRIMEX.

Retention aid R3 was a cationic quaternary ammonium maize starch, sold by Corn Products Limited under the Trade Name of Q TAC.

Retention aid R4 was a 28 percent by weight solution of a nitrogen containing cationic polyelectrolyte sold by Stockhausen under the Trade Name of STOCKHAUSEN K225FL.

Retention aid R5 was a 10 percent by weight solution of an epichlorhydrin modified polyamide sold by Hercules Powder Co., Delaware, under the Trade Name KYMENE 557.

Retention aid R6 was a solid nitrogen containing cationic polymer of the polyelectrolyte type sold by Allied Colloids under the Trade Name PERCOL 292.

The cyclic imide sizes were as follows:-
S1, N-stearoyl succinimide; S2, N-stearoyl glutarimide;
S3, N-acetyl hexadecyl succinimide (comparison imide); S4,
S5, S6 and S7 respectively N-lauroyl, N-myristoyl, N-palmitoyl and N-behenoyl succinimide and S8, N-stearoyl-4-cyclohexene-1, 2-dicarboximide.

The components of the emulsions A to AA are summarised in Table 1, and the sizing ability of the emulsions is given in Table 2.

Table 1

| | S1 | S2 | S3 | S4 | S5 | S6 | S7 | S8 | pH |
|---|---|---|---|---|---|---|---|---|---|
| A | 1.1 | — | — | | | | | | 4:5 |
| B | — | — | 1.1 | | | | | | |
| C | — | 1.1 | — | | | | | | |
| D | 1.1 | — | — | | | | | | 3:8 |
| E | 1.1 | | | | | | | | 3:3 |
| F | 1.1 | | | | | | | | |
| G | 1.1 | | | | | | | | 3:3 |
| H | 1.1 | | | | | | | | |
| I | 1.1 | | | | | | | | |
| J | 1.1 | | | | | | | | |
| K | 1.1 | | | | | | | | |
| L | 1.1 | | | | | | | | |
| M | 1.1 | | | | | | | | |
| N | 1.1 | | | | | | | | |
| P | 1.1 | | | | | | | | |
| Q | 1.1 | | | | | | | | |
| R | 1.1 | | | | | | | | |
| S | | | | 1.1 | | | | | |
| T | | | | | 1.1 | | | | |
| U | | | | | | 1.1 | | | |
| V | 1.1 | | | | | | | | |
| W | | | | | | | 1.1 | | |
| X | | | | | | | | 1.1 | |
| Y | | | | | | | | 1.1 | |
| Z | | | | | | | | 1.1 | |
| AA | | | | | | | | 1.1 | |

| | E1 | E2 | E3 | E4 | R1 | R2 | R3 | R4 | R5 | R6 |
|---|---|---|---|---|---|---|---|---|---|---|
| A | 0.02 | 0.03 | — | — | | | 0.55 | | | |
| B | — | — | 0.1 | — | | | 0.55 | | | |
| C | 0.02 | 0.03 | — | — | | | 0.55 | | | |
| D | 0.08 | 0.12 | — | 0.1 | | | 0.55 | | | |
| E | 0.2 | 0.3 | — | — | | | 0.55 | | | |
| F | 0.02 | 0.03 | — | — | | | 0.55 | | | |
| G | 0.2 | 0.3 | — | — | | | 0.55 | | | |
| H | 0.2 | 0.3 | — | — | 0.03 | — | 0.55 | | | |
| I | 0.2 | 0.3 | — | — | — | 0.02 | 0.55 | | | |
| J | 0.2 | 0.3 | | | | | 0.55 | 0.01 | | |
| K | 0.2 | 0.3 | | | | | 0.55 | 0.02 | | |
| L | 0.2 | 0.3 | | | | | 0.55 | 0.03 | | |
| M | 0.2 | 0.3 | | | | | 0.55 | 0.04 | | |
| N | 0.2 | 0.3 | | | | | 0.55 | 0.05 | | |
| P | 0.2 | 0.3 | | | | | | 0.03 | | |
| Q | 0.2 | 0.3 | | | | | | 0.05 | | |
| R | 0.2 | 0.3 | | | | | | 0.07 | | |
| S | 0.2 | 0.3 | | | | | 0.55 | | | |
| T | 0.2 | 0.3 | | | | | 0.55 | | | |
| U | 0.2 | 0.3 | | | | | 0.55 | | | |
| V | 0.2 | 0.3 | | | | | 0.55 | | | |
| W | 0.2 | 0.3 | | | | | 0.55 | | | |
| X | 0.2 | 0.3 | | | | | 0.55 | 0.11 | | |
| Y | 0.2 | 0.3 | | 0.03 | | | 0.55 | | | |
| Z | 0.2 | 0.3 | | | | | 0.55 | | 0.03 | |
| AA | 0.2 | 0.3 | | | | | 0.55 | | | 0.03 |

Table 2

| Emulsion | Addition Level | Cobb Value 2.5 mins. drying | Addition Level | Cobb Value 8.75 mins drying |
|---|---|---|---|---|
| A | 0.18 | 32 | 0.19 | 27 |
| | 0.29 | 26 | 0.30 | 25 |
| | 0.40 | 21 | 0.41 | 19 |
| | 0.58 | 20 | 0.57 | 18 |
| B | 0.14 | 70 | 0.19 | 65 |
| | 0.24 | 80 | 0.25 | 73 |
| | 0.37 | 64 | 0.37 | 53 |
| C | 0.30 | 80 | 0.30 | 45 |
| | 0.46 | 60 | 0.46 | 30 |
| | 0.54 | 65 | 0.60 | 27 |
| D | 0.16 | 73 | 0.17 | 45 |
| | 0.25 | 26 | 0.28 | 25 |
| | 0.31 | 24 | 0.32 | 22 |
| E | 0.09 | 74 | 0.09 | 64 |
| | 0.17 | 70 | 0.18 | 64 |
| | 0.28 | 26 | 0.28 | 30 |
| | 0.32 | 23 | 0.36 | 20 |
| | 0.47 | 23 | 0.47 | 20 |
| F | 0.2 | 32 | 0.2 | 27 |
| | 0.3 | 26 | 0.3 | 25 |
| | 0.4 | 21 | 0.4 | 19 |
| | 0.5 | 20 | 0.5 | 18 |
| H | 0.18 | 26 | 0.17 | 21 |
| | 0.26 | 21 | 0.26 | 20 |
| | 0.31 | 19 | 0.36 | 16 |
| I | 0.1 | 53 | 0.1 | |
| | 0.19 | 33 | 0.19 | 22 |
| | 0.32 | 20 | 0.32 | 19 |
| J | .09 | 47 | | |
| | .19 | 25 | | |
| | .26 | 21 | | |
| | .38 | 21 | | |
| K | 0.12 | 37 | | |
| | 0.20 | 18 | | |
| | 0.31 | 18 | | |
| L | 0.11 | 21 | | |
| | 0.20 | 18 | | |
| | 0.32 | 17 | | |

Table 2-continued

| Emulsion | Addition Level | Cobb Value 2.5 mins. drying | Addition Level | Cobb Value 8.75 mins drying |
|---|---|---|---|---|
| M | 0.05 | 59 | | |
|   | 0.09 | 22 | | |
| N | 0.05 | 42 | | |
|   | 0.10 | 21 | | |
| P | 0.05 | 70 | 0.05 | 65 |
|   | 0.09 | 64 | 0.10 | 45 |
|   | 0.20 | 21 | 0.20 | 19 |
|   | 0.27 | 19 | 0.27 | 18 |
| Q | 0.05 | 67 | 0.04 | 61 |
|   | 0.12 | 28 | 0.11 | 24 |
|   | 0.20 | 20 | 0.20 | 18 |
| R | 0.05 | 61 | 0.05 | 52 |
|   | 0.10 | 24 | 0.10 | 22 |
|   | 0.19 | 20 | 0.20 | 18 |
| X | 0.075 | 38 | | 2.5 mins drying |
|   | 0.09 | 22 | | |
| Y | 0.042 | 74 | 0.045 | 72 |
|   | 0.085 | 33 | 0.09 | 32 |
| Z | 0.043 | 57 | 0.046 | 55 |
|   | 0.079 | 23 | 0.08 | 23 |
|   | 0.156 | 17 | 0.166 | 18 |
| AA | 0.044 | 63 | 0.046 | 60 |
|   | 0.09 | 20 | 0.095 | 16 |

In Table 3 the Cobb Values quoted were achieved after the handsheets had been dried for 2.5 minutes at 110° C.

Table 3

| Addition Level | Cobb values after drying for 2.5 mins at 110° C. | | | | |
|---|---|---|---|---|---|
|   | S | T | U | V | W |
| 0.2 | 65 | — | 57 | 49 | 54 |
| 0.25 | 65 | — | 53 | 33 | 32 |
| 0.3 | 65 | 80 | 45 | 25 | — |
| 0.35 | 65 | — | 33 | 22 | 21 |
| 0.4 | 65 | 70 | 24 | — | — |

From Table 2 it can be seen that over a 10 fold range of the concentrations of the emulsifiers suitable sizing was achieved by N-stearoyl succinimide, and that sizing improved as the concentration was raised. The advantage of the retention aids can be seen by a comparison of the results for emulsions J to N, and for emulsions P to Q. Using J to N the results clearly show that as the amount of the second aid is increased, whilst keeping the other constituents of the emulsions the same, the % w/w addition level required to give a selected level of sizing falls e.g. from about 0.26 percent using J to 0.10% using N each to give a Cobb Value of 21. Using P to R, the trend is slightly less clear, but comparing 0.09/0.10 percent addition level for P and R show Cobb results of 64 and 45 for P, but 24 and 22 for R, I.e. R is close to full sizing whereas P has not even reached half sizing.

From a comparison of the results obtained using emulsions B with those obtained using any other of the emulsions A and O to R it can be seen that the sizing achieved by N-acetyl hexadecyl succinimide was very poor and that it was not significantly improved when the curing/drying stage was 8.75 minutes. Thus the succinimide size in which the acyl was only a short chain, but the ring carried the hydrophobic group was much worse than the N-acylated succinimide in which the acyl group contained the hydrophobic group.

From a comparison of the results using emulsion C with those using emulsion A, and D to R it can be seen that substituted succinimide was a better size than the corresponding substituted glutarimide but that sizing using the glutarimide could occur provided a sufficient period of curing/drying was allowed.

From the results given in Table 2 it can be seen that sizing markedly improved as the length of the hydrophobic group was increased from $C_{14}$ (myristoyl) to $C_{16}$ (palmitoyl) and the improvement tailed off from $C_{18}$ (stearoyl) to $C_{20}$ (behenoyl).

It will also be seen that, the results obtained using N-stearoyl-4-cyclohexene-1,2-dicarboximide compared favourably with all the other cyclic imides tested in Example 1 sizing to about Cobb 20 being obtainable with addition levels of 0.09 to 0.16 percent by weight.

EXAMPLE 2

In this Example the storage stability of the emulsion G was tested, and the results are summarised in Table 4. The addition level was calculated on the basis of the original concentration of N-stearoyl succinimide in the emulsion.

Table 4

| Age of emulsion in days | Addition Level | Cobb value after drying for 2.5 mins at 110° C |
|---|---|---|
| 0 | 0.32 | 24 |
| 1 | 0.35 | 24 |
| 2 | 0.30 | 25 |
| 3 | 0.32 | 25 |
| 4 | 0.34 | 21 |
| 5 | 0.38 | 23 |
| 10 | 0.41 | 23 |
| 15 | 0.35 | 22 |
| 21 | 0.31 | 23 |
| 25 | 0.33 | 22 |
| 40 | 0.34 | 22 |
| 42 | 0.42 | 19 |

Form Table 4 it will be seen that the results obtained within the limits of experimental error of the Cobb Test demonstrate that the sizing ability of the emulsion had not altered markedly during storage for up to 6 weeks.

EXAMPLE 3

In this Example the paper pulp was sized in the presence of calcium carbonate filler to determine its compatibility with N-stearoyl succinimide sizing. The emulsion used had the same components as emulsion L, the retention aid K225FL being added after size and carbonate addition, and the pH in the handsheet machine was 8.

The results are summarised in Table 5.

Table 5

| $CaCO_3$ | Addition Level | Cobb Value 2.5min/100° C | Addition Level | Cobb Value 8.75min/100° C |
|---|---|---|---|---|
| 10% | 0.16 | 34 | 0.15 | 28 |
|   | 0.22 | 22 | 0.25 | 21 |
|   | 0.30 | 20 | 0.32 | 19 |
| 5% | 0.15 | 28 | 0.17 | 24 |
|   | 0.24 | 20 | 0.26 | 18 |

Table 5-continued

| CaCo₃ | Addition Level | Cobb Value 2.5min/100° C | Addition Level | Cobb Value 8.75min/100° C |
|---|---|---|---|---|
| | 0.32 | 17 | 0.31 | 18 |

The results in Table 5 show that N-stearoyl succinimide can successfully size in the presence of up to 10 percent calcium carbonate, and that sizing still occurs rapidly.

EXAMPLE 4

In Example 4 handsheets of paper, prepared by the general method described hereinbefore save for the addition of size, were contacted for one minute with a solution of the size in dichloromethane. The handsheets picked up their own weight of solution and hence variation in the addition level was achieved by variation in the concentration of the solution. The wet handsheets were allowed to lose solvent by evaporation and were then dried for the period of time and in the manner indicated in Table 6. In one set of experiments the handsheets were dried for 2.5 minutes at 110° C in a drum drier. In the second set they were additionally dried for 10 minutes in an oven at 110° C. The sheets were then conditioned under the standard conditions of 20° C and 65 percent relative humidity, for 30 minutes, and tested for water repellancy using the Cobb Test. The results of the test are summarised in Table 6. Experiments with hexadecyl succinimide (SA), and N-methyl hexadecyl succinimide (SB) are included by way of comparison only.

Table 6

| Size | Addition Level | Cobb Values after drying in Drum | Drum & Oven |
|---|---|---|---|
| Hexadecyl succinimide SA | 0.01 | 61 | 49 |
| | 0.02 | 54 | 49 |
| | 0.03 | 57 | 49 |
| | 0.04 | 57 | 50 |
| N-methyl hexadecyl succinimide SB | 0.01 | 59 | 60 |
| | 0.02 | 58 | 56 |
| | 0.03 | 59 | 54 |
| | 0.04 | 58 | 44 |
| N-acetyl hexadecyl succinimide SC | 0.01 | 58 | 58 |
| | 0.02 | 55 | 52 |
| | 0.03 | 53 | 38 |
| | 0.04 | 51 | 23 |
| N-stearoyl succinimide SD | 0.005 | 60 | |
| | 0.01 | 34 | |
| | 0.02 | 27 | |
| | 0.03 | 24 | |
| N stearoyl glutarimide SE | 0.005 | 60 | |
| | 0.01 | 55 | |
| | 0.02 | — | |
| | 0.03 | 52 | |
| N-stearoyl phthalimide SF | 0.005 | 88 | |
| | 0.01 | 74 | |
| | 0.02 | 92 | |
| | 0.03 | 84 | |
| N-stearoyl-3,6-endoxo-4-cyclohexene-1,2-dicarboximide SG | 0.01 | 67 | |
| | 0.02 | 28 | |
| | 0.03 | 22 | |
| N-stearoyl cyclohexane-1,2-dicarboximide SH | 0.01 | 38 | |
| | 0.02 | 22 | |
| | 0.03 | 22 | |
| N-stearoyl-4-cyclohexene-1,2-dicarboximide SI | 0.01 | 42 | |
| | 0.02 | 23 | |
| | 0.03 | 20 | |

EXAMPLE 5

In this Example the storage stability of an emulsion prepared by the general method described in Example 1 and containing 1.1 g N-stearoyl-4-cyclohexene-1,2-dicarboximide, 0.2g of emulsifier E1, 0.3g of E2 and 0.55g of E3 and made up to 100 mls with water. The emulsion had a pH of 5.2. Retention aid R5 (0.03 percent by weight) was added to the paper pulp in the disintegrator.

Table 7

| Age of emulsion days | Addition Level | Cobb Value after drying for 2.5 mins. at 110° C. |
|---|---|---|
| 0 | .093 | 22 |
| 14 | .085 | 21 |
| 48 | .09 | 23 |
| 80 | .10 | 20 |
| 102 | .10 | 21 |
| 180 | .10 | 21 |

EXAMPLE 6

In this Example emulsions were prepared using an APV Manton Gaulin Model 15M-8BA single stage piston homogeniser.

The emulsions were prepared by heating for 15 minutes at 90° C a liter of water containing 60 gms cationic starch or 120 gms of polyamide-polyamine epichlorhydrin condensate (referred to as PAE) or 60 gms of each, as indicated in Table 8, and then adding at 90° C 120 grams of N-stearoyl-4-cyclohexene-1,2-dicarboximide with vigorous stirring. The crude emulsion was then homogenised at 2–3000 psi, diluted with cold water to give a product containing 6 percent by weight of size and cooled to ambient temperature. The cold emulsion was then passed through the homogeniser until it had attained a viscosity of below 150 centipoise.

The emulsion contained retention aid R7, a cationic starch commercially available from Laing National Ltd. under the Trade Name CATO 8, or retention aid R3. PAE was prepared by the method described in Example 1 and 2 of BP 865727.

Paper handsheets were prepared and sized by the general method described for Examples 1 to 5, the paper being made from the type of pulp indicated in Table 8. In every experiment except the one denoted by an asterisk, 0.03 percent by weight of retention aid R4 was added to the pulp in the disintegrator.

Table 8

| Emulsion containing | Pulp | Addition Level | Cobb Value after drying at 110°C. | | | |
|---|---|---|---|---|---|---|
| | | | 1.5 | 2.0 | 2.5 | 3.0 |
| R7 PAE | BERGVIC | 0.05 | 27 | 25 | 23 | 22 |

Table 8-continued

| Emulsion containing | Pulp | Addition Level | Cobb Value after drying at 110°C. | | |
|---|---|---|---|---|---|
| | | | 1.5 | 2.0 | 2.5 | 3.0 |
| R7 | " | 0.075 | 26 | 24 | 24 | 24 |
| R7 | " | 0.1 | 23 | 21 | 22 | 22 |
| R7 | " | 0.05 | 41 | 32 | 37 | 29 |
| R3 | " | 0.05 | 69 | 55 | 59 | 39 |
| PAE | " | 0.05 | 31 | 26 | 26 | 25 |
| R7 PAE | KAJAANI | 0.1 | 32 | 31 | 25 | 23 |
| R7 | " | 0.1 | 34 | 26 | 25 | 23 |
| R7 PAE | STORA 32 | 0.075 | 29 | 28 | 27 | 27 |
| R7 | " | 0.1 | 28 | 29 | 32 | 27 |
| R7 | KAUKAS | 0.1 | 31 | 30 | 31 | 26 |
| R7 PAE* | MECHANICAL | 0.25 | 27 | 23 | 23 | 22 |
| R7 | " | 0.35 | 37 | 35 | 24 | 23 |

From Table 8 it can be seen that paper made from a wide range of paper pulps could be sized adequately using compositions according to the present invention.

EXAMPLE 7

In this Example emulsions were prepared by the method described in Example 6. The weight ratios of N-stearoyl-4-cyclohexene-1,2-dicarboximide to retention aid R7 and PAE were respectively 2:1 and 1:1, except the results denoted by * where they were 1:1 and 2:1. The aqueous paper pulps indicated in Table 9 were then sized in a pilot plant paper machine at pH 8 producing a 480 mm wide sheet at a rate of 6.1 m/min with basis weight of 60 grams per square meter. In all experiments 0.03 percent by weight retention aid R4 was added to the mixing box of the machine flow system, the emulsion being added at the same point, but through a separate inlet. Cobb values were measured on samples taken at the reel of the paper machine, as the paper was produced, and then after a period of 1 or 5 days ageing.

Table 9

| Emulsion containing | Pulp | Addition Level | Cobb Value after days ageing | | |
|---|---|---|---|---|---|
| | | | 0 | 1 | 5 |
| R7 | BERGVIC | 0.15 | 24 | 29 | 20 |
| R7 PAE | " | 0.1 | 25 | 21 | 19 |
| R7 PAE | " | 0.075 | 40 | 38 | 24 |
| R7 | KAJAANI | 0.175 | 42 | 27 | — |
| R7 PAE * | " | 0.15 | 25 | 18 | 16 |
| R7 PAE * | " | 0.125 | 38 | 20 | 19 |
| R7 | STORA 32 | 0.075 | 27 | 26 | 27 |
| PAE | " | 0.1 | 24 | 23 | 20 |
| PAE | " | 0.075 | 32 | 28 | 24 |
| R7 PAE | " | 0.075 | 24 | 23 | 21 |

EXAMPLE 8

Preparation of N-stearoyl-4-cyclohexene-1,2-dicarboximide

A solution of 4-cyclohexene-1,2-dicarboximide (151g) and triethylamine (300 mls) in dichloropropane (900 mls) was maintained at a temperature of 50° C during the addition thereto over a period of 10 minutes, with constant stirring, of a solution of stearoyl chloride (302.5g) in a dichloropropane (300 mls). The mixture was stirred at 50° C for a further period of 10 minutes during which time triethylamine hydrochloride precipitated out, and was then filtered hot. The filtered precipitate was then washed with small portions of hot dichloropropane and the washings were combined with the filtrate. The solvent from the combined washings and filtrate was then evaporated off in a rotary evaporator to yield solid N-stearoyl-4-cyclohexene-1,2-dicarboximide, which was recrystallised from 60° – 80° petroleum ether.

We claim:

1. A composition for treating cellulosic materials selected from the group consisting of cellulose, regenerated cellulose and mixtures thereof, comprising a dispersion of a reactive sizing or waterproofing agent in a liquid medium wherein the said reactive sizing or waterproofing agent is a cyclic imide substituted by an aliphatic hydrophobic group containing at least 12 carbon atoms and N-substituted by an acyl group.

2. A composition according to claim 1 wherein the cyclic imide is represented by the general formula:

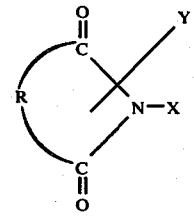

wherein R represents a diradical completing a 5 or 6 membered ring, Y represents the aliphatic hydrophobic radical and X represents the acyl group.

3. A composition according to claim 2 wherein X and Y are combined to form an N-subsstituent in which the aliphatic hydrophobic group is linked to the N-atom through a carbonyl group and R is selected from the group consisting of dimethylene and non-aromatic carbocyclic diradicals.

4. A composition according to claim 2 wherein the aliphatic hydrophobic group contains from 16 to 22 carbon atoms.

5. A composition according to claim 2 wherein the dispersion is an aqueous emulsion containing a retention aid in a weight ratio of retention aid to cyclic imide of from 2:1 to 1:50.

6. A composition according to claim 5 wherein the retention aid is a polyacrylamide.

7. A composition according to claim 5 wherein the aqueous emulsion contains additionally an emulsifying agent in a weight ratio of emulsifying agent to cyclic imide of from 1:1 to 1:50.

8. A composition according to claim 5 wherein the cyclic imide is free of ethylinic unsaturation conjugated to each carbonyl group in the primary imide ring.

9. A composition according to claim 1 wherein the cyclic imide is a non-aromatic cyclic imide substituted by an aliphatic hydrophobic group and N-substituted by an acyl group.

10. A process for treating a cellulosic material selected from the group consisting of cellulose, regenerated cellulose, and mixtures thereof, comprising the step of contacting the cellulosic material with a dispersion of a sizing or waterproofing quantity of a cyclic imide which is represented by the general formula:

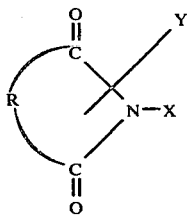

wherein R represents a diradical completing a 5 or 6 membered ring, Y represents an aliphatic hydrophobic radical containing at least 12 carbon atoms and X represents an acyl group.

11. A process according to claim 10 wherein X and Y are combined to form an N-substituent in which the aliphatic hydrophobic group is linked to the N-atom through a carbonyl group.

12. A process according to claim 10 wherein the dispersion is an aqueous emulsion containing a retention aid in a weight ratio to the cyclic imide of from 2:1 to 1:50.

13. A process according to claim 12 wherein the cellulosic material is aqueous paper stock having a pH of from 4 to 10.

14. A process according to claim 13 wherein the aqueous paper stock contains carbonate as a filler and is alkaline.

15. A process according to claim 13 wherein the aqueous paper stock is mechanical pulp.

16. A process for the preparation of an N-acylated cyclic imide having the general formula:

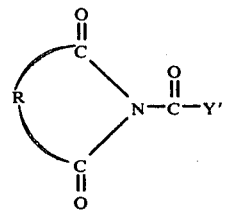

wherein R represents a diradical completing a 5 or 6 membered ring, and Y' represents an aliphatic hydrophobic radical containing at least 11 carbon atoms, comprising the steps of reacting a cyclic imide having the general formula:

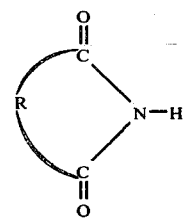

wherein R represents the diradical defined hereinbefore, with a long chain acyl chloride containing at least 12 carbon atoms and in the presence of at least one mole of a short chain tertiary amine per mole of the lesser molar quantity of the acyl chloride or cyclic imide, in solution at a temperature of from 0° C to 100° C thereby forming insoluble tertiary amine hydrochloride and soluble N-acylated cyclic imide, maintaining the reaction until at least some tertiary amine hydrochloride has precipitated out of solution, and recovering N-long chain-acylated cyclic imide from the solution.

17. A process according to claim 16 wherein the tertiary amine is triethylamine and the solvent is dichloropropane.

18. A cyclic imide which is represented by the formula:

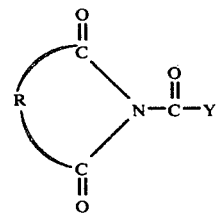

wherein R represents a non-aromatic carbocyclic diradical and Y an aliphatic hydrophobic group containing at least 11 carbon atoms.

19. A cyclic imide according to claim 18 wherein Y contains from 15 to 21 carbon atoms and R is a cyclohexyl or cyclohexenyl diradical.

* * * * *